United States Patent [19]

Chan

[11] Patent Number: 4,517,132

[45] Date of Patent: May 14, 1985

[54] PROCESS FOR PREPARATION OF CYANOHYDRINS

[75] Inventor: John K. Chan, Raleigh, N.C.

[73] Assignee: Union Carbide Corporation, Danbury, Conn.

[21] Appl. No.: 509,135

[22] Filed: Jun. 29, 1983

[51] Int. Cl.$^3$ .................. C07C 121/75; C07C 121/36
[52] U.S. Cl. .............................. 260/465 F; 260/465.6
[58] Field of Search .......................... 260/465 F, 465.6

[56] References Cited

U.S. PATENT DOCUMENTS 2,175,805  10/1939  Jacobson ...................... 260/465.6 X
2,731,490  1/1956   Barsky ............................. 260/465.6
2,794,042  5/1957   Tanona et al. .................... 260/465.6

OTHER PUBLICATIONS

Scorah et al., Chem. Abstracts, vol. 29, 814, (1935).
Wilson, Chem. Abstracts, vol. 31, 417, (1937).
Farbenind, Chem. Abstracts, vol. 31, 2615, (1937).
Roessler, Chem. Abstracts, vol. 32, 958, (1938).
Organic Syntheses, Collective vol. II, 7, (1941).
Lucas et al., J. Am. Chem. Soc., vol. 59, 1682, (1937).
Boekelheide et al., J. Am. Chem. Soc., vol. 72, 712, (1950).
Organic Syntheses, vol. 20, 43, (1940).

Primary Examiner—Dolph H. Torrence
Attorney, Agent, or Firm—Gerald L. Coon

[57] ABSTRACT

This invention relates to the discovery that high yields of excellent quality cyanohydrins can be prepared by reacting certain carbonyl compounds in a solution of metallic cyanide and hydrochloric acid.

8 Claims, No Drawings

PROCESS FOR PREPARATION OF CYANOHYDRINS

FIELD OF THE INVENTION

This invention relates to a novel method of preparing high yields of cyanohydrins which are useful intermediates in the production of insecticidally active compounds.

BACKGROUND OF THE INVENTION

Cyanohydrins are important starting materials which can be used to synthesize precursors for insecticidally active compounds.

For example, 2-hydroxy-3-methylbutyronitrile, can be used as the starting material in the synthesis of 2-methyl-3-cyano-3-(ethylpropylthiophosphoryloxy)propane, an extremely active insecticide.

The procedure for the preparation of cyanohydrins calls for the addition of hydrogen cyanide to carbonyl compounds as follows:

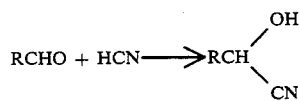

wherein R can be hydrogen, alkyl, haloalkyl, alkoxyalkyl, aryl, alkylaryl, haloaryl, or alkoxyaryl.

The reaction is generally accomplished by reacting the carbonyl compound with liquid hydrogen cyanide in the presence of a basic catalyst as set forth in British Pat. Nos. 416,007 and 452,285; and French Pat. Nos. 804,124 and 812,366. The reaction is reversible and the cyanohydrin product is usually stabilized by acidification before isolation.

In U.S. Pat. No. 2,731,490, a continuous method for the production of cyanohydrins by passing gaseous hydrogen cyanide to a mixture of an aldehyde or ketone and an aqueous alkali solution followed by adjusting the mixture's pH to 7 is described. Other similar production methods employing gaseous hydrogen cyanide as starting reactant are described in U.S. Pat. Nos. 2,175,805 and 2,794,042.

A more convenient method to prepare cyanohydrins is to generate hydrogen cyanide in the reaction mixture by the action of sulfuric, nitric, phosphoric, or acetic acid on an alkali cyanide in the presence of a carbonyl compound as set forth for example in Organic Synthesis, Coll. Vol. II, 7 (1941); Lucas and Prater, J. Am. Chem. Soc., 59, 1682 (1937); Colonge and Joly, Ann. Chim., (11) 18, 303 (1943); Ultee, Rec. Trav. Chim., 28, 1, 248 (1909); and Boekelheide and Schilling, J. Am. Chem. Soc., 72, 712 (1950).

Alternatively, as set forth in Organic Syntheses, Volume 20, 43 (1940), an alkali bisulfite can also be employed to react with a carbonyl compound to form a bisulfite addition product, which is then reacted with alkali cyanide to form the desired cyanohydrin.

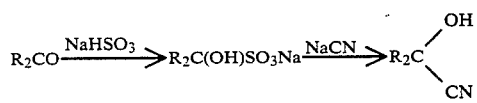

Although these conventional methods are effective, they only afford moderate yields of reaction products. Furthermore, the cyanohydrin products obtained from the above prior art procedures require additional purification steps in order to realize a commercially acceptable quality product. For example, as described in Organic Synthesis, Collective Volume II (page 7) supra, the synthesis of acetone cyanohydrin from acetone, sodium cyanide, and diluted sulfuric acid afforded only 77–78% yield of product which had to purified by vacuum distillation.

Consequently, there exists a need for a more efficient and economical process for the production of cyanohydrins.

SUMMARY OF THE INVENTION

In accordance with the present invention, it has now been discovered that high yields of excellent quality cyanohydrin products can be realized by the use of hydrochloric acid in the in situ generation of hydrogen cyanide for the cyanohydrin syntheses.

The general reaction is shown as follows:

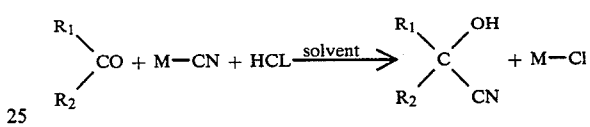

The organic groups designated by the symbols $R_1$ and $R_2$ are intended to include individually hydrogen, alkyl, haloalkyl, alkoxyalkyl, aryl, alkylaryl, haloaryl or alkoxyaryl and M designates an alkali metal.

DETAILED DESCRIPTION OF THE INVENTION

The invention relates to the discovery that high yields of excellent quality cyanohydrins can be prepared by reacting certain carbonyl compounds in a solution of metallic cyanide and hydrochloric acid.

The overall reaction method for the preparation of the cyanohydrins comprises (a) reacting a compound of Formula A (A)

wherein $R_1$ and $R_2$ are individually hydrogen, alkyl, haloalkyl, alkoxyalkyl, aryl, alkylaryl, haloaryl or alkoxyaryl, with (B) a metallic cyanide; and (C) hydrochloric acid; in the presence of a solvent; and (b) recovering the cyanohydrin.

Examples of the preferred carbonyl compounds in the reaction of this invention are formaldehyde, acetaldehyde, propionaldehyde, isobutyraldehyde, chloroacetaldehyde, N-caproaldehyde, acetone, methyl ethyl ketone, methyl isobutyl ketone, chloroacetone, and hexanone-3.

The preferred metallic cyanides as represented by M—CN in the above formula, are potassium cyanide, sodium cyanide and calcium cyanide.

Water is the most preferred solvent for this cyanohydrin synthesis since it is inexpensive and has the advantage that most of the reactants are soluble therein.

Other preferred solvent systems are methanol, ethanol, isopropanol, methylene chloride, toluene, mixtures thereof, as well as aqueous mixtures of the solvent systems.

The preferred amount of metallic cyanide to be employed is 5 to 75 weight percent based on the solvent system. The most preferred amounts of the alkali cyanide to be present in the reaction system is 10–40 weight percent based on the solvent. More solvent can, of course, be used, however, the excess quantities of solvent provide only higher dilution of the solvent mass and serve no particular benefits.

Best results are obtained when equimolar amounts of the metallic cyanide, hydrochloric acid, and the appropriate carbonyl compound are used. However, a slight excess of any of these reactans will not affect the reaction efficiency.

The temperature for the reaction may range from −20° to 30° C.; with the preferred range being −10+ to 10° C. The reaction is conducted satisfactorily under atmospheric pressure; however, somewhat higher or lower pressures do not adversely affect the product yield.

When the reaction is conducted at −10° to 10° C., a time of 2 to 10 hours is required for completion. The most preferred reaction time is 2 to 6 hours.

Under the preferred conditions, the carbonyl compound is fed slowly into the solvent system containing the alkali cyanide followed by the slow addition of hydrochloric acid. When the feed time of the carbonyl compound particularly the aldehydes, is too short the product yield is significantly reduced. Under preferred conditions, longer times do not affect the cyanohydrin efficiency.

The general procedure for the syntheses of this invention involves slowly feeding a solution of the carbonyl compound at 0° to 5° C. to a solvent mixture, preferably an aqueous mixture, containing the metallic cyanide, the addition being made over a 1–2 hour period followed by an additional hour of stirring. A calculated amount of hydrochloric acid is then added to the reaction mixture over a period of 2–3 hours at the same reaction temperature. After an additional stirring period of 30 minutes, the reaction mixture is extracted with methylene chloride at ambient temperature. The organic extract, after drying over magnesium sulfate, is evaporated under reduced pressure to give the desired cyanohydrin as a residual product. The crude product is obtained in high quality and is directly acceptable for other reactions.

The metallic chloride by-products formed with the process of this invention are extremely soluble in water and less soluble in the cyanohydrin products than the by-products of the prior art processes such as the potassium bisulfite by-product produced when sulfuric acid is used. As a result, the metallic chlorides are readily removed from the reaction mixture.

The following examples are set forth for the purposes of illustrations so that those skilled in the art may better understand the invention, and it should be understood that these examples are not to be construed as limiting this invention in any matter.

EXAMPLE I

Synthesis of 2-Hydroxy-3-methylbutyronitrile

Isobutyraldehyde (70.2 g, 0.97 mole) was added dropwise to a stirred aqueous mixture containing sodium cyanide (48 g, 0.98 mole) in 116 g of water, the addition being made over a 1.0 hour period at 0° to 5° C. After the addition was completed, the reaction mixture was stirred for one hour longer at 0° to 5° C. A solution of 37% hydrochloric acid (96.5 g, 0.98 mole) was then fed into the reaction mixture at 0° to 5° C. over a period of 2.5 hours. After stirring for an additional 0.5 hour period, the reaction mixture was extracted twice with methylene chloride. The organic extracts, after drying over magnesium sulfate, was concentrated under reduced pressure to give 89.2 g of excellent-quality product, which was identified by spectral analyses as 2-hydroxy-3-methylbutyronitrile. The product yield was 92.4% based on the amount of isobutyraldehyde used.

EXAMPLE II

Synthesis of Acetone Cyanohydrin

Procedure: Under the same conditions as described in Example I, when anhydrous acetone (60 g, 1.03 mole) was used to react with sodium cyanide (48 g, 0.98 mole), and hydrochloric acid (37%, 96.5 g, 0.98 mole) followed by methylene chloride extraction, the resulting product was isolated in 87.6% yield and was identified as acetone cyanohydrin by spectral analysis.

Comparative Example of Acetone Cyanohydrin Synthesis Using Literature-Described Procedure Procedure: Using the same procedure as described in Organic Synthesis, Collective Vol. II, page 7, a mixture of 500 g of sodium cyanide in 1.2 liters of water and 900 ml of acetone was placed in a 5-liter reaction flask. Keeping the reaction temperature at 10°–20° C., 2.1 liters of 40% sulfuric acid was added over a period of three hours. When the addition was completed, the mixture was stirred for 15–20 minutes longer and then the flask was set aside for the salt to settle. The organic layer was separated by decantation and the sodium bisulfate salt was removed by filtration and was washed with three 50-ml portions of acetone. The combined filtrate and acetone washings were added to the aqueous solution, which was then extracted three times with 250-ml portions of ether. The extracts were combined with the cyanohydrin previously separated by decantation and dried with anhydrous sodium sulfate. The ether and unreacted acetone were removed by atmospheric distillation and the residue was distilled under reduced pressure. The product fraction, boiling at 78°–82° C./15 mm was collected weighting 640 g which was identified as acetone cyanohydrin. The product yield, based on sodium cyanide, was 77.6%.

EXAMPLE III

Synthesis of Methyl Ethyl Ketone Cyanohydrin

Procedure: The process of Example I was repeated using methyl ethyl ketone (72.1 g, 1.0 mole) as starting material. A quantity of 87 g of product, identified as methyl ethyl ketone cyanohydrin, was obtained. The product yield was 88.9% based on the amount of methyl ethyl ketone used.

EXAMPLE IV

Synthesis of 2-Hydroxy-n-valeronitrile

Procedure: The process of Example 1 was repeated using n-butyraldehyde (70.2 g, 0.97 mole) as starting material. A quantity of 81.3 g of product, identified as 2-hydroxy-n-valeronitrile, was obtained. The product yield was 84.6% based on the amount of butyraldehyde used.

EXAMPLE V

Pilot Plant-Scale Synthesis of 2-Hydroxy-3-Methylbutyronitrile

Procedure: The process of Example I was repeated on a pilot-plant scale using 35.2 pounds of isobutyraldehyde and 31.8 pounds of potassium cyanide as starting materials in 70 pounds of water with 59 pounds of a 37% solution of hydrochloric acid. After the similar work-up, a quantity of 43.5 pounds of excellent-quality 2-hydroxy-3-methylbutyronitrile was obtained. The product yield was 90 percent based on isobutyraldehyde.

I claim:

1. A method of preparing cyanohydrins which comprises:
(a) reacting a compound of Formula A
(A)

wherein $R_1$ and $R_2$ are individually hydrogen, alkyl, haloalkyl, alkoxyalkyl, aryl, alkylaryl, haloaryl or alkoxyaryl; with
(B) a metallic cyanide; and
(c) hydrochloric acid; in the presence of a solvent; and
(b) recovering the cyanohydrin.

2. A method of preparing cyanohydrins which comprises:
(a) reacting a compound of Formula A
(A)

wherein $R_1$ and $R_2$ are individually hydrogen; $C_1$–$C_6$ alkyl, haloalkyl, alkoxyalkyl; phenyl, $C_1$–$C_6$ alkylphenyl, halophenyl or $C_1$–$C_6$ alkoxyphenyl, with
(B) a metallic cyanide and
(C) hydrochloric acid; in the presence of a solvent; and
(b) recovering the cyanohydrin.

3. A method according to claim 2 wherein said metallic cyanide is selected from the group consisting of sodium cyanide; potassium cyanide; and calcium cyanide.

4. A method according to claim 1 wherein
$R_1$ and $R_2$ are individually hydrogen; $C_1$–$C_6$ alkyl or haloalkyl; and
said metallic cyanide is sodium cyanide or potassium cyanide.

5. A method according to claim 1 wherein said solvent is selected from the group consisting of water, methanol, ethanol, isopropanol, methylene chloride, toluene and mixtures thereof.

6. A method according to claim 1 wherein said solvent is water.

7. A method of preparing cyanohydrins which comprises:
(a) reacting a compound of Formula A
(A)

wherein $R_1$ and $R_2$ are individually hydrogen, alkyl, haloalkyl, alkoxyalkyl, aryl, alkylaryl, haloaryl, or alkoxyaryl, with
(B) from about 5 to 75 weight percent based on the total mixture of a metallic cyanide; and
(C) hydrochloric acid at a reaction temperature of from about $-20°$ C. to about $30°$ C. in the presence of a solvent; and
(b) recovering the cyanohydrin.

8. A method according to claim 7 wherein
said metallic cyanide is present from about 10 to about 40 weight percent based on the total mixture;
said solvent is water; and
said reaction temperature is from about $-10°$ C. to about $10°$ C.

* * * * *